United States Patent
Antonini

(10) Patent No.: US 8,492,547 B2
(45) Date of Patent: Jul. 23, 2013

(54) METHOD FOR THE ENRICHMENT OF BUPRENORPHINE USING CHROMATOGRAPHIC TECHNIQUES

(75) Inventor: Enrico A. Antonini, Edwardsville, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 327 days.

(21) Appl. No.: 12/818,230

(22) Filed: Jun. 18, 2010

(65) Prior Publication Data
US 2011/0009633 A1  Jan. 13, 2011

Related U.S. Application Data
(60) Provisional application No. 61/224,083, filed on Jul. 9, 2009.

(51) Int. Cl.
*C07D 471/00* (2006.01)
*C07D 489/12* (2006.01)
*C07D 491/00* (2006.01)
*C07D 498/00* (2006.01)
*C07D 513/00* (2006.01)
*C07D 515/00* (2006.01)
*C07D 489/00* (2006.01)
*A61K 31/44* (2006.01)

(52) U.S. Cl.
USPC ............... 546/39; 546/46; 514/279; 514/282

(58) Field of Classification Search
CPC .... C07D 471/00; C07D 489/12; C07D 491/00; C07D 498/00; C07D 513/00; C07D 515/00; C07D 489/00; C07D 489/08; A61K 31/44
See application file for complete search history.

(56) References Cited

U.S. PATENT DOCUMENTS

| 7,671,203 B2 * | 3/2010 | Antonini | 546/44 |
| 2005/0182257 A1 | 8/2005 | Antonini | |
| 2007/0293676 A1 | 12/2007 | Antonini | |

FOREIGN PATENT DOCUMENTS

WO   WO 03/074526 A1 *  9/2003

OTHER PUBLICATIONS

Mostafavi, A. et al. Development and validation of a HPLC method for the determination of buprenorphine hydrochloride, naloxone hydrochloride and noroxymorphone in a tablet formulation. Talanta. 2009, vol. 77, p. 1416.*
Harris, D.C. Quantitative Chemical Analysis 7th Edition. WH Freeman and Company, New York. 2007, p. 575-580.*
Galand et al., "OPLC and AMD, Recent Techniques of Planar Chromatography: Their Interest for Separation and Characterization of Extractive and Synthetic Compounds", Fitoterapie, 73(2), 2002, XP 002599422.

* cited by examiner

*Primary Examiner* — Janet Andres
*Assistant Examiner* — Ben S Michelson

(57) ABSTRACT

The present invention provides processes for the enrichment of buprenorphine in a product. In particular, the present invention provides processes for the enrichment of buprenorphine in a product using chromatographic techniques.

20 Claims, No Drawings

METHOD FOR THE ENRICHMENT OF BUPRENORPHINE USING CHROMATOGRAPHIC TECHNIQUES

CROSS REFERENCE TO RELATED APPLICATIONS

This application claims the benefit of U.S. Provisional Application No. 61/224,083 filed Jul. 9, 2009, which is incorporated herein in its entirety.

FIELD OF THE INVENTION

The present invention generally relates to processes for the enrichment of buprenorphine in a product. In particular, the present invention relates to processes for the enrichment of buprenorphine in a product using chromatographic techniques.

BACKGROUND OF THE INVENTION

Buprenorphine is a semi-synthetic opiate with partial agonist and antagonist actions. As such, it is a powerful analgesic that is approximately twenty-five to forty times as potent as morphine and is indicated for the treatment of moderate to severe chronic pain or for pre-operative analgesia. Buprenorphine is also used to treat opiate addiction. Accordingly, the demand for buprenorphine is increasing. Processes for synthesizing buprenorphine have been known since the late 1960s; it is traditionally made from either thebaine or oripavine in seven or more steps. Not only is the overall yield low (typically less than 10%), but the final product has levels of impurities that exceed the currently prescribed guidelines established by the International Conference on Harmonisation of Technical Requirements for Registration of Pharmaceuticals for Human Use (ICH) and the United States Pharmacopeial Convention (USP).

More efficient processes are being developed to increase the yield of buprenorphine while minimizing the formation of side products, and to ensure that the final product has a level of purity that meets current ICH and USP standards. However, even the more efficient processes may still be relatively ineffective at avoiding or eliminating side products that are chemically similar to the desired buprenorphine product. For example, side products of buprenorphine synthesis such as Impurity A (2-[17-(but-3-enyl)-4,5α-epoxy-3-hydroxy-6-methoxy-

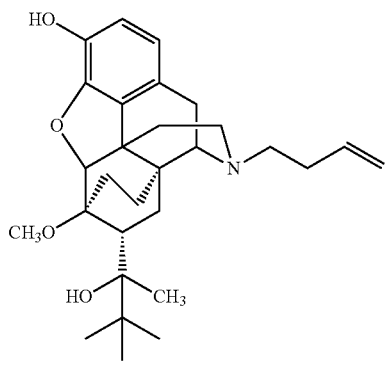

(I)

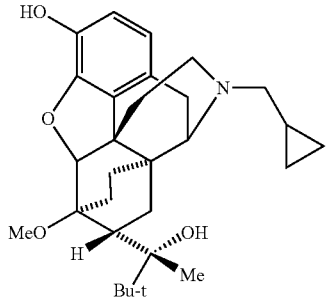

(II)

6α) having Formula (I) above is similar chemically to buprenorphine, shown above as Formula (II)

Impurity A may be formed during the synthesis of buprenorphine, and is difficult to separate from the desired buprenorphine product using existing techniques such as liquid phase separation and crystallization due to the similar chemical structure and properties of Impurity A to buprenorphine. A need exists for a method of eliminating chemically similar side products from crude buprenorphine, resulting in a final product with a level of purity that meets current ICH and USP standards.

SUMMARY OF THE INVENTION

The present invention provides processes for the enrichment of buprenorphine in a product. In particular, the present invention provides processes for the enrichment of buprenorphine in a product using chromatographic techniques.

One aspect of the present invention encompasses a method for enriching buprenorphine relative to 2-[17-(but-3-enyl)-4,5α-epoxy-3-hydroxy-6-methoxy-6α,14-ethano-14α-morphinan-7α-yl]-3,3-dimethylbutan-2-ol and 17-(cyclopropylmethyl)-α-(1,1-dimethylethyl)-4,5-epoxy-3-hydroxy-6-methoxy-α-methyl-6,14-ethenomorphinan-7-methanol in a buprenorphine product. The method includes forming a first feed solution by dissolving a crude buprenorphine composition in a solvent mixture. The crude buprenorphine composition includes buprenorphine, 2-[17-(but-3-enyl)-4,5α-epoxy-3-hydroxy-6-methoxy-6α,14-ethano-14α-morphinan-7α-yl]-3,3-dimethylbutan-2-ol, and 17-(cyclopropylmethyl)-α-(1,1-dimethylethyl)-4,5-epoxy-3-hydroxy-6-methoxy-α-methyl-6,14-ethenomorphinan-7-methanol in a solvent mixture. The solvent mixture includes an acid, a first organic polar solvent, and water.

The method further includes contacting the first feed solution with a stationary phase and introducing a first mobile phase into the stationary phase. The second mobile phase includes a second organic solvent and water. The amount of the second solvent in the first mobile phase is at least 85% by volume.

The method additionally includes eluting a first product fraction from the stationary phase. The first product fraction includes between about 80% and 100% of the amount of buprenorphine contained in the crude buprenorphine composition.

Other features and iterations of the invention are described in more detail below.

DETAILED DESCRIPTION

The present invention provides a method for enriching buprenorphine in a buprenorphine product using preparative reversed phase chromatography. In particular, processes have been discovered that enrich the buprenorphine relative to impurities such as Impurity A, which exhibits chemical properties that are similar to those of buprenorphine. Another approach focuses on removing color only when such impurities are not present. The method includes forming a feed solution by dissolving a crude buprenorphine composition in a solvent mixture, contacting the feed solution with a stationary phase, introducing into the stationary phase a mobile phase, and eluting from the stationary phase a product fraction that includes from about 80% to 100% of the amount of buprenorphine contained in the crude buprenorphine composition. A buprenorphine base solid may be additionally formed by evaporating a fraction of the mobile phase from the product fraction and adding an amount of a proton-acceptor in order to raise the pH of the evaporated product fraction to a pH of about 9.

The method may further include forming a buprenorphine salt and a mother liquor by combining the buprenorphine base solid with an organic solvent such as isopropanol and a salt-forming agent such as hydrochloric acid. The mother liquor includes dissolved buprenorphine, the organic solvent, and the salt-forming agent remaining after removing the buprenorphine salt.

The method may also include eluting a first recycle fraction from the stationary phase prior to eluting the product fraction and eluting a second recycle fraction from the stationary phase after eluting the product phase.

The method may additionally include forming a second feed solution by evaporating at least one of the first recycle fraction, the second recycle fraction, the mother liquor, or combinations thereof. The second feed solution may be contacted with the stationary phase, a second mobile phase may be introduced into the stationary phase, and a second product fraction may be eluted from the stationary phase. An additional amount of buprenorphine base solid may be formed by evaporating an amount of the second mobile phase from the second product fraction and adjusting the pH of the resulting slurry to about 9 by the addition of a proton-accepting agent such as ammonium hydroxide. An additional amount of buprenorphine salt may be formed by dissolving the buprenorphine base solid in an organic solvent such as isopropyl alcohol and a salt-forming agent such as hydrochloric acid.

(I) Feed Solution

The feed solution is formed by dissolving a crude buprenorphine composition in a solvent mixture. The crude buprenorphine composition may include buprenorphine as well as at least one impurity that may possess similar chemical properties to buprenorphine. Non-limiting examples of impurities in the crude buprenorphine composition include Impurity A (2-[17-(but-3-enyl)-4,5α-epoxy-3-hydroxy-6-methoxy-6α,14-ethano-14α-morphinan-7α-yl]-3,3-dimethylbutan-2-ol), Impurity B (2-(4,5α-epoxy-3-hydroxy-6-methoxy-6α,14-ethano-14α-morphinan-7α-yl)-3,3-dimethylbutan-2-ol), Impurity C (4,5α-epoxy-7α-[(1S)-1-hydroxy-1,2,2-trimethylpropyl]-3,6-dimethoxy-6α,14-ethano-14α-morphinan-17-carbonitrile), Impurity D (17-(cyclopropylmethyl)-α-(1,1-dimethylethyl)-4,5-epoxy-3-hydroxy-6-methoxy-α-methyl-6α,14-ethanomorphinan-7-methanol), and Impurity E (2-[17-(cyclopropylmethyl)-4,5α-epoxy-3,6-dihydroxy-6α,14-ethano-14α-morphinan-7α-yl]-3,3-dimethylbutan-2-ol).

The solvent mixture includes an amount of an acid, an amount of a first organic polar solvent, and water. The composition of the solvent mixture is selected to completely dissolve the buprenorphine in the crude buprenorphine composition and to prevent the dissolved buprenorphine from precipitating in the feed solution while the feed solution is contacted with the stationary phase. In addition, the composition of the solvent mixture is selected so as not to inhibit the adsorption of the buprenorphine to the stationary phase.

Non-limiting examples of an acid include acetic acid, malic acid, tartaric acid, sulfuric acid, formic acid, oxalic acid, lactic acid, hydrochloric acid, hydrobromic acid, phosphoric acid, phosphorous acid, nitric acid and combinations thereof. In an exemplary embodiment, the acid is acetic acid.

In one exemplary embodiment, if the acid is acetic acid, the amount of acid contained in the solvent mixture ranges from about 0.1% to about 5% by volume. In other embodiments, if the acid is acetic acid, the amount of acid contained in the solvent mixture may range from about 0.1% to about 1%, from about 0.5% to about 1.5%, from about 1% to about 2%, from about 1.5% to about 2.5%, from about 2% to about 3%, from about 2.5% to about 3.5%, from about 3% to about 4%, from about 3.5% to about 4.5%, and from about 4% to about 5% by volume.

Non-limiting examples of the first organic polar solvent include ethanol, methanol, propanol, isopropanol, butanol, t-butanol, acetonitrile and combinations thereof. In an exemplary embodiment, the first organic polar solvent is methanol.

In one embodiment, the amount of the first organic polar solvent contained in the solvent mixture ranges from about 20% to about 80% of the total volume of the solvent mixture. In other embodiments, the solvent mixture ranges from about 20% to about 30%, from about 25% to about 35%, from about 30% to about 40%, from about 35% to about 45%, from about 40% to about 50%, from about 45% to about 55%, from about 50% to about 60%, from about 55% to about 65%, from about 60% to about 70%, and from about 65% to about 75%, and from about 70% to about 80% of the total volume of the solvent mixture. In an exemplary embodiment, the amount of the first organic solvent is about 40% by volume. In another exemplary embodiment, the amount of the first organic solvent is about 60% by volume.

In one embodiment, the concentration of crude buprenorphine composition in the solvent mixture ranges from about 10 g of crude buprenorphine composition to about 100 g of crude buprenorphine composition per L of solvent mixture. In other embodiments, the concentration of crude buprenorphine composition in the solvent mixture ranges from about 10 g to about 20 g, from about 15 g to about 25 g, from about 20 g to about 30 g, from about 25 g to about 35 g, from about 30 g to about 40 g, from about 35 g to about 45 g, from about 40 g to about 50 g, from about 45 g to about 55 g, from about 50 g to about 60 g, from about 55 g to about 65 g, from about 60 g to about 70 g, from about 65 g to about 75 g, from about 70 g to about 80 g, from about 75 g to about 85 g, from about 80 g to about 90 g, from about 85 g to about 95 g, and from about 90 g to about 100 g of crude buprenorphine composition per L of solvent mixture.

The feed solution may be formed using known mixing techniques including but not limited to mixing, stirring, agitating, swirling, and shaking. The temperature at which the formation of the feed mixture occurs may range from about 20° C. to about 70° C. The pH at which the feed solution is formed may range from about 2 to about 8. In an exemplary embodiment, the feed solution may be formed by agitating the crude buprenorphine composition in the solvent mixture at a temperature ranging from about 35° C. to about 50° C., and a pH ranging from about 3.5 to about 5. In order to maintain the dissolution of the buprenorphine in the feed solution, the feed solution may be maintained at a temperature ranging from about 25° C. to about 50° C. until the feed solution is contacted with the stationary phase.

In another embodiment, undissolved solids from the crude buprenorphine composition may be optionally separated from the feed solution prior to contacting the feed solution with the stationary phase. The undissolved solids may be separated using known techniques including but not limited to filtering and centrifuging. In an exemplary embodiment, the feed solution may be filtered with a Whatman no. 4 membrane prior to introducing the feed solution to the stationary phase. In another exemplary embodiment, the feed solution may be filtered with a 0.45 µm nylon membrane prior to introducing the feed solution to the stationary phase.

In one embodiment, the total volume of the feed solution may range from about 50 mL to about 100 L mL depending on a variety of factors including the load ratio, the volume of the chromatography column, and the amount of time allocated to the buprenorphine enrichment process. In an exemplary embodiment, the volume of the feed solution is from about 1,000 mL to about 1,500 mL.

The volumetric rate at which the feed solution is contacted with the stationary phase may range from about 1 mL/min to about 12 L/min depending on a variety of factors including the volume of the stationary phase, the composition of the stationary phase, and the length and diameter of the chromatography column in which the stationary phase is packed. In an exemplary embodiment, the feed solution is contacted with the stationary phase at a volumetric flow rate of about 200 mL/min.

(II) Stationary Phase

As the feed solution is contacted with the stationary phase, the dissolved buprenorphine and impurities such as Impurity A having similar chemical properties to buprenorphine adsorb to the stationary phase. The stationary phase is selected to possess surface chemical properties with a high affinity for adsorbing the dissolved buprenorphine and impurities from the feed solution. In addition, the stationary phase is selected to possess surface properties that have slightly different affinities for the buprenorphine relative to the impurities such that the buprenorphine and impurities are eluted from the stationary phase at different times, making possible the fractionation of the buprenorphine from the impurities.

In one embodiment, the stationary phase includes a plurality of approximately spherical particles ranging from about 1 micron to about 200 microns in diameter. In other embodiments, the particles of the stationary phase range from about 1 micron to about 40 microns, about 20 microns to about 60 microns, about 40 microns to about 80 microns, about 60 microns to about 100 microns, about 80 microns to about 120 microns, about 100 microns to about 140 microns, about 120 microns to about 160 microns, about 140 microns to about 180 microns, and about 160 microns to about 200 microns in diameter. In an exemplary embodiment, the particles of the stationary phase are about 20 microns in diameter. In another embodiment, the particles are about 130 microns in diameter.

The particles of the stationary phase may also contain pores ranging from about 50 Å to about 300 Å in diameter. In other embodiments, the particles of the stationary phase may contain pores ranging from about 50 Å to about 150 Å, from about 100 Å to about 200 Å, from about 150 Å to about 250 Å, and from about 200 Å to about 300 Å in diameter. In an exemplary embodiment, the particles of the stationary phase contain pores with a diameter of about 120 Å.

The stationary phase may include particles made of materials including but not limited to alkylsilanes, arylsilanes, haloalkylsilanes, alkyl esters, aryl esters, alkyl amines, alkylcyano compounds, alkyldiols, alkyl ethers, aryl ethers, haloalkyl ethers, alkylcarboxylic acids, arylcarboxylic acids, alkysulfonic acids, arylsulfonic acids, polystyrenedivinylbenzene, aminopolycaprolactem, and mixtures thereof. Other stationary phase materials may include silica, polymers, zirconium oxide or titanium. To enhance the affinity of the surface of the stationary phase particles for buprenorphine, each particle may additionally include a plurality of ligands. The ligands are attached to the exposed surface of the stationary phase particles and are selected to possess a selectively high binding affinity for the dissolved buprenorphine in the feed solution, as well as the ability to elute the buprenorphine in a separate fraction form any other impurities present in the feed solution. Suitable ligands include octadecyl (C18) ligands, octyl (C8) ligands, butyl (C4) ligands, tricosane (C23) ligands, cyano groups, phenyl groups, and mixtures thereof. In an exemplary embodiment, the stationary phase particles are silica with attached octadecyl ligands.

A critical aspect of the method of the present invention is the loading ratio, defined herein as the mass of stationary phase contacted with the feed solution relative to the mass of buprenorphine dissolved in the feed solution. If the load ratio is too low, the separation of the phase containing the pure buprenorphine may not be sufficient to collect suitably enriched buprenorphine during elution. If the load ratio is too high, the buprenorphine may elute in a separate peak, but the increased amount of stationary phase required would render this method of buprenorphine enrichment economically unfeasible.

In one embodiment, the load ratio used ranges from about 0.02 grams to about 1000 grams of stationary phase per gram of buprenorphine dissolved in the feed solution. In other embodiments, the load ratio ranges from about 0.02 grams to about 0.20 grams, from about 0.10 to about 2 grams from about 1 gram to about 20 grams, 10 grams to about 200 grams, from about 100 grams to about 300 grams, from about 200 grams to about 400 grams, from about 300 grams to about 500 grams, from about 400 grams to about 600 grams, from about 500 grams to about 700 grams, from about 600 grams to about 800 grams, from about 700 grams to about 900 grams, and from about 800 grams to about 1000 grams of stationary phase per gram of buprenorphine dissolved in the feed solution. In an exemplary embodiment, the load ratio ranges from about 20 g to about 40 g of stationary phase per gram of buprenorphine dissolved in the feed solution. In another embodiment, the load ratio ranges from 0.02 to 0.10 g of stationary phase per gram of buprenorphine dissolved in the feed solution.

In an embodiment, the stationary phase may be packed into a high-performance preparative liquid chromatography column with a diameter ranging from about 0.1 cm to about 200 cm. In other embodiments, the diameter of the high-performance preparative liquid chromatography column may range from about 0.1 cm to about 40 cm, about 20 cm to about 60 cm, about 40 cm to about 80 cm, about 60 cm to about 100 cm, about 80 cm to about 120 cm, about 100 cm to about 140 cm, about 120 cm to about 160 cm, about 140 cm to about 180 cm, and about 160 cm to about 200 cm. The length of the high-performance preparative liquid chromatography column may range from about 10 cm to about 100 cm. In other embodiments, the length of the high-performance preparative liquid chromatography column may range from about 10 cm to about 30 cm, from about 20 cm to about 40 cm, from about 30 cm to about 50 cm, from about 40 cm to about 60 cm, from about 50 cm to about 70 cm, from about 60 cm to about 80 cm, from about 70 cm to about 90 cm, and from about 80 cm to about 100 cm. In an exemplary embodiment, the stationary phase is packed into a high-performance preparative liquid chromatography column with a length of about 25 cm and a diameter of about 1 cm.

Prior to contact with the feed solution, the stationary phase may be immersed in an organic polar solvent including but not limited to ethanol, methanol, propanol, isopropanol, butanol, t-butanol, acetonitrile and combinations thereof. In an exemplary embodiment, the stationary phase is immersed in methanol prior to contact with the feed solution. The organic solvent may be mixed with an acid including but not limited to acetic acid, malic acid, tartaric acid, sulfuric acid, formic acid, oxalic acid, lactic acid, hydrochloric acid, hydrobromic acid, phosphoric acid, phosphorous acid, nitric acid and combinations thereof.

In one exemplary embodiment, if the acid is acetic acid, the amount of acid contained in the solvent mixture ranges from about 0.1% to about 10% by volume. In other embodiments, if the acid is acetic acid, the amount of acid contained in the solvent mixture may range from about 0.1% to about 1%, from about 0.5% to about 1.5%, from about 1% to about 2%, from about 1.5% to about 2.5%, from about 2% to about 3%, from about 2.5% to about 3.5%, from about 3% to about 4%, from about 3.5% to about 4.5%, from about 4% to about 5%, from about 5.5% to about 6.5%, from about 5.5% to about 6.5%, from about 6.5% to about 7.5%, from about 7% to about 8%, from about 7.5% to about 8.5%, from about 8% to about 9%, from about 8.5% to about 9.5%, and from about 9% to about 10% by volume.

In an exemplary embodiment, the stationary phase is immersed in methanol prior to contact with the feed solution. In another embodiment, the stationary phase is immersed in a mixture that contains 95% methanol and 5% acetic acid.

After contact with the feed solution and elution of the various fractions, the stationary phase may be recycled and used for the enrichment of buprenorphine from additional amounts of crude buprenorphine composition. Prior to reuse, the stationary phase is immersed in an organic solvent including but not limited to ethanol, methanol, propanol, isopropanol, butanol, t-butanol, acetonitrile and combinations thereof. In an exemplary embodiment, the stationary phase is immersed in methanol after introducing the mobile phase into the stationary phase and obtaining the various elution fractions, and reused for subsequent enrichment of buprenorphine in a buprenorphine product. In another embodiment, the stationary phase is immersed in 95% methanol and 5% acetic acid after introducing the mobile phase into the stationary phase and obtaining the various elution fractions, and reused for subsequent enrichment of buprenorphine in a buprenorphine product. The presence of the acetic acid is necessary to ensure that any color that was adsorbed is removed. This will not occur with the organic solvent alone.

(III) Mobile Phase

The mobile phase is introduced into the stationary phase in order to deadsorb the buprenorphine from the stationary phase, and elute the buprenorphine as a product fraction that includes the buprenorphine dissolved in the mobile phase. The composition of the mobile phase is selected to be capable of eluting the buprenorphine as a product fraction that is distinct from the fractions containing other eluates such as Impurity A.

In one embodiment, the mobile phase includes a second organic polar solvent and water. The second organic polar solvent may include, but is not limited to ethanol, methanol, propanol, isopropanol, butanol, t-butanol, acetonitrile and combinations thereof. In an exemplary embodiment, the mobile phase includes methanol and water.

The amount of second organic polar solvent in the mobile phase affects the rate at which the buprenorphine is eluted from the stationary phase, and the fractionation of the buprenorphine from impurities such as Impurity A. The higher the proportion of second organic solvent in the mobile phase, the more rapidly the buprenorphine is eluted from the stationary phase, resulting in less distinct fractionation of buprenorphine from the other eluted impurities. In one embodiment, the amount of the second organic polar solvent ranges from about 20% to about 100% of the volume of the mobile phase. In other embodiments, the amount of the second organic polar solvent ranges from about 20% to about 30%, from about 25% to about 35%, from about 30% to about 40%, from about 35% to about 45%, from about 40% to about 50%, from about 45% to about 55%, from about 50% to about 60%, from about 55% to about 65%, from about 60% to about 70%, from about 65% to about 75%, from about 70% to about 80%, from about 75% to about 85%, from about 80% to about 90%, from about 85% to about 95%, and from about 90% to about 100% of the volume of the mobile phase. In an exemplary embodiment, the mobile phase includes about 90% methanol and about 10% water by volume.

The concentration of the second organic polar solvent in the mobile phase introduced into the stationary phase may be constant throughout the elution of the buprenorphine and impurity fractions, or the concentration of the second organic solvent may vary. The concentration of the second organic polar solvent in the mobile phase may change gradually over a period ranging from about 30 seconds to about 30 minutes, or the concentration may change essentially instantaneously over a period of less than about five seconds.

The volumetric rate at which the mobile phase is introduced into the stationary phase may range from about 1 mL/min to about 500 mL/min depending on a variety of factors including the volume of the stationary phase, the composition of the stationary phase, and the length and diameter of the chromatography column into which the stationary phase is packed. In an exemplary embodiment, the mobile phase is introduced into the stationary phase at a volumetric flow rate of about 200 mL/min.

The cumulative amount of mobile phase that is introduced into the stationary phase may range from about 1,000 mL to about 300 L depending on a variety of factors including the volume of the feed solution introduced into the stationary phase, the load ratio, and the composition of the mobile phase. In an exemplary embodiment, if the volume of the feed solution is about 1,200 mL, the amount of mobile phase introduced into the stationary phase is about 5,000 mL.

(IV) Fractions Eluted From Stationary Phase

The contact of the feed solution with the stationary phase causes the dissolved buprenorphine and other impurities to adsorb to the surface of the stationary phase particles. Subsequent introduction of mobile phase into the stationary phase causes the buprenorphine and other impurities to deadsorb from the stationary phase and dissolve into the mobile phase. Because the surface of the stationary phase has a different binding affinity for the buprenorphine than for the impurities, the buprenorphine typically desorbs from the stationary phase at a different time than the time at which the impurities desorb. As a result, fractions of the total eluate that are desorbed from the stationary phase may be collected at different times. Each separate fraction typically contains a different proportion of buprenorphine relative to other impurities.

The concentration of buprenorphine and impurities in the eluate may be monitored using measurements known in the art including UV absorbance, mass spectrometric analysis, visual color, electrical conductance, and density. In an exemplary embodiment, the concentration of buprenorphine and impurities in the eluate is monitored by measuring the UV absorbance of the eluate at wavelengths of 280 nm and 300 nm.

As the eluate emerges from the stationary phase after introducing the mobile phase into the stationary phase, the buprenorphine content of the eluate follows a stereotypical time course. As an illustrative example, the initial eluate contains essentially no buprenorphine, as evidenced by the lack of UV absorbance of the eluate. As more eluate emerges, the UV absorbance of the eluate increases to a value above some minimal threshold, indicating the buprenorphine has started to deadsorb from the stationary phase. The buprenorphine concentration of the eluate slowly increases until the UV absorbance level rapidly increases above a second concentration level, indicating that the majority of the buprenorphine is desorbing from the stationary phase. The buprenorphine concentrate of the emerging eluate increases to a peak level and then gradually decreases until the UV absorbance decreases below a second threshold level, indicating that relatively little buprenorphine is left to desorb from the stationary phase. Eventually, the concentration of buprenorphine in the emerging eluate drops below detectable levels.

In one embodiment, the product fraction of the eluate may be collected and subjected to further processing. The product fraction, as defined herein, is the fraction of the eluate containing from about 80% to 100% of the total buprenorphine contained in the feed solution. Further, the mass ratio of buprenorphine to combined impurities may range from about 95:5 to about 99.99:0.01. In an exemplary embodiment, the mass ratio of buprenorphine to combined impurities ranges from about 99.5:0.5 to about 99.99:0.01. In another exemplary embodiment, the mass ratio of buprenorphine to combined impurities ranges from about 99.0:1.0 to about 99.99:0.01.

In one illustrative example, the product fraction may be collected from the time that the UV detection of buprenorphine sharply increases above a threshold level to the time that the UV detection of buprenorphine in the emerging eluate falls below a second threshold level. In this embodiment, the elution period at which the product fraction is collected corresponds to a time at which buprenorphine is desorbing from the stationary phase, and the other impurities have either previously desorbed or have yet to desorb.

In another embodiment, a first recycle fraction and a second recycle fraction may be collected in addition to the product fraction. The first recycle fraction may contain from about 1% to about 20% of the total buprenorphine in the feed solution, and the second recycle fraction may contain from about 1% to about 20% of the buprenorphine in the feed solution. In addition, the mass ratio of buprenorphine to combined impurities in the first and/or second recycle fraction may be less than about 99.5:0.5.

The eluate fractions are typically subjected to at least one post-enrichment process in order to recover the buprenorphine from the eluate fractions. The first and second recycle fractions typically contain unacceptably high concentrations of one or more impurities such as Impurity A and must undergo additional buprenorphine enrichment. In one embodiment, the first and second recycle fractions are subjected to an evaporation process, described below, to reduce the amount of organic polar solvent in the recycle fractions. The buprenorphine contained in the product fraction may be recovered using post-enrichment processes including but not limited to evaporation, precipitation and the formation of buprenorphine salts.

(V) Post-Enrichment Processes

The eluate fractions may undergo one or more post-enrichment processes to recover the buprenorphine contained in these fractions. The post-enrichment processes include evaporation, precipitation, formation of buprenorphine salts, and recycling. Evaporation reduces the amount of organic polar solvent in a mixture such as an elution fraction or a mother liquor. The formation of buprenorphine salts transforms a quantity of buprenorphine base solids into a quantity of buprenorphine salts. Recycling subjects a byproduct of the enrichment process such as the first or second recycle fractions or other byproducts such as the mother liquor to a second chromatographic treatment using the previously described buprenorphine enrichment process.

(a) Evaporation

The eluate fractions may undergo evaporation to reduce the concentration of organic polar solvent in the eluate fractions. Evaporation subjects an eluate fraction to a combination of temperature and pressure that results in the vaporization of at least a fraction of the organic polar solvent contained in the eluate fraction without significantly evaporating the water contained in the eluate fraction. In one embodiment, the eluate fractions may be evaporated at a temperature ranging from about 60° C. to about 70° C., and at a vacuum pressure ranging between about 250 mbar and about 400 mbar of vacuum. In another embodiment, the mother liquor resulting from a buprenorphine salt formation process may be subjected to evaporation using similar temperature and pressure conditions to those described above.

The length of the evaporation process may vary depending on a variety of factors including subsequent processes to which the evaporated fraction is to be subjected. For example, if the evaporated fraction is a product fraction to be subjected to precipitation, the length of evaporation may be selected to result in a concentration of organic polar solvent in the evaporated product fraction of about 0.1% to about 50% by volume. If the evaporated fraction is a recycle fraction to be recycled back through the stationary phase or the mother liquor from a buprenorphine salt formation process, the evaporation may be conducted until a slurry forms.

The evaporated fraction may be additionally subjected to precipitation or recycling depending on the fraction. For example, an evaporated product fraction is subjected to precipitation in one embodiment. In another example, an evaporated recycle fraction or evaporated mother liquor is recycled. In one embodiment, about 1 mL of acetic acid is added to the evaporated product fraction after the vacuum is removed before subjecting the evaporated product fraction to precipitation.

(b) Precipitation

After evaporation or after the product is collected from the column, the product fraction may be precipitated to form a dried buprenorphine base solid. In one embodiment, an amount of ammonium hydroxide sufficient to reduce the pH if the evaporated product fraction to a pH ranging from 8.0 to 10 is added to the evaporated product fraction, forming a slurry. The resulting slurry is cooled to less than 25° C. and the resulting solids are transferred to a conventional filtering apparatus, and water is used to rinse any remaining solids from the precipitation vessel into the filtering apparatus. The solids in the filtering apparatus are washed with additional water and then dried in a vacuum oven at a temperature ranging from about 50° C. to about 70° C. and a pressure ranging from 0 mbar to about 350 mbar for at least 14 hours. The buprenorphine base solids formed in the precipitation process may be further subjected to a buprenorphine salt formation process.

(c) Buprenorphine Salt Formation

The dried buprenorphine base solids may be subjected to a buprenorphine salt formation process in which the dried buprenorphine base solids are contacted with a salt-forming agent. In this process, the dried buprenorphine base solids are dissolved in an organic polar solvent. Non-limiting examples of organic non-polar solvents include ethanol, methanol, propanol, isopropanol, butanol, t-butanol, acetonitrile and combinations thereof. In an exemplary embodiment, the organic polar solvent is isopropanol. The temperature of the solution may be increased to a temperature ranging from about 40° C. to about 70° C. to attain full dissolution of the buprenorphine base solids.

Once the buprenorphine base solid is dissolved in the organic polar solvent, an amount of salt-forming agent is added. Non-limiting examples of salt-forming agents include hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalic acid, fumaric acid, propionic acid, aspartic acid, glutamic acid, benzoic acid, methyl fluoride, methyl chloride, methyl bromide, and methyl iodide. In an exemplary embodiment, the salt-forming agent is hydrochloric acid.

As an illustrative example, if the organic polar solvent is isopropanol, the dried buprenorphine base solids are dissolved using about 16.2 mL of isopropanol per gram of buprenorphine base solid and heated to a temperature ranging from about 40° C. to about 50° C. Once the solids are dissolved, 37 weight % (v/v) HCl is added to the solution in the amount of about 0.26 g of 37% HCl for every gram of buprenorphine. The mixture is cooled to less than 20° C. and the resulting solids are separated from the mother liquor by filtration. After rinsing with fresh isopropanol, the filtered solids are then dried in a vacuum oven at a temperature ranging from about 50° C. to about 70° C. and a pressure ranging from 0 mbar to about 350 bar for at least 14 hours.

The mother liquor may contain up to about 10% by weight of the buprenorphine in the buprenorphine base solids. In one embodiment, the mother liquor may be treated with a proton-acceptor such as ammonium hydroxide to raise the pH of the mother liquor to above 7. The resulting mixture may then be subjected to evaporation as described above.

(d) Recycling

In one embodiment, a second feed solution may be formed from the byproducts of the original buprenorphine enrichment process and recycled through a second round of buprenorphine enrichment. The second feed solution may include the evaporated first recycle fraction, the evaporated second recycle fraction, the evaporated mother liquor, and combinations thereof. The second feed solution includes dissolved buprenorphine and dissolved impurities such as Impurity A. In one embodiment, the feed solution is maintained at a temperature ranging from about 30° C. to about 40° C. and a pH ranging from about 4.5 to about 5.

The second feed solution is contacted with the stationary phase in a manner similar to that of the first feed solution. Prior to contact with the second feed solution, the stationary phase may be reactivated by immersing the stationary phase in an organic polar solvent including but not limited to ethanol, methanol, propanol, isopropanol, butanol, t-butanol, acetonitrile and combinations thereof.

Once the second feed solution has been contacted with the stationary phase, a second mobile phase is introduced into the stationary phase. The composition of the second mobile phase is similar to the mobile phase described in Section III above. In one embodiment, the second mobile phase includes an organic polar solvent and water. The organic polar solvent may include, but is not limited to ethanol, methanol, propanol, isopropanol, butanol, t-butanol, acetonitrile and combinations thereof. In an exemplary embodiment, the mobile phase includes methanol and water.

The buprenorphine and impurity content of the eluate is monitored using a UV detector, as described in Section IV above and used to determine when to initiate and terminate the collection of a second product fraction. During recycling, only a second product fraction is collected and retained; no recycle fractions are collected during recycling. The second product fraction may be subjected to additional post-enrichment processes including but not limited to evaporation and buprenorphine salt formation.

(VI) Exemplary Embodiment

In an exemplary embodiment, a feed solution is formed by dissolving an amount of crude buprenorphine composition into a sufficient amount of solvent mixture to yield a concentration of about 27 g of crude buprenorphine composition per L of solvent mixture. In this exemplary embodiment, the solvent mixture contains about 48% methanol, about 48% deionized water, and about 4% glacial acetic acid by volume. While agitating to dissolve the crude buprenorphine composition, the mixture is heated to a temperature ranging from about 35° C. to about 50° C. After filtering the mixture, the resulting feed solution is maintained at a temperature ranging from about 35° C. to about 40° C. to maintain dissolution.

The feed solution is contacted with a stationary phase at a load ratio ranging from about 20 g to about 40 g of stationary phase per gram of buprenorphine contained in the crude buprenorphine composition. The stationary phase is made up of a plurality of 20 μm silica particles containing pores with a diameter of about 120 Å and a plurality of octadecyl ligands attached to the surface of the particles. The stationary phase is packed into a chromatographic column that is about 8 cm long and about 1 cm in diameter.

The mobile phase is introduced into the stationary phase after the feed solution has contacted the stationary phase. In this exemplary embodiment, the mobile phase contains about 90% methanol and about 10% water by volume. The resulting eluate is monitored using a UV detector set to wavelengths of 280 nm and 300 nm. A first recycle fraction, first product fraction, and second recycle fraction are collected for post-enrichment processing.

The product fraction is evaporated at a temperature ranging from about 60° C.-70° C. and a vacuum pressure ranging from about 250 mbar to about 400 mbar until a slurry appears. After removing the vacuum pressure, acetic acid is added to the evaporated product fraction at about 1 mL per gram of buprenorphine in the product fraction.

The evaporated product fraction is precipitated by adding 29 weight % ammonium hydroxide to increase the pH of the evaporated product fraction to a pH of about 9 at a temperature ranging from about 35° C. to about 50° C. The resulting slurry is cooled to a temperature below about 15° C., and the buprenorphine base solids are filtered from the slurry, using deionized water to transfer any remaining solids from the precipitation container into the filter and to rinse the filtered solids in the filter. The filtered buprenorphine base solids are then dried in a vacuum oven for at least 2 hours at a temperature ranging from about 50° C. to about 70° C. and a vacuum pressure ranging from 0 mbar and about 350 mbar.

Buprenorphine salts are formed from the dried buprenorphine base solids by dissolving the solids in isopropanol in the amount ranging from about 16 mL to about 17 mL of isopropanol per gram of buprenorphine in the buprenorphine base solids, and heating the mixture to a temperature ranging from about 40° C. to about 50° C. A 37 weight % hydrochloric acid solution by volume is added to the heated mixture as a salt-forming agent in an amount ranging from about 0.20 g to about 0.30 g of HCl solution per g of buprenorphine in the heated mixture. The resulting mother liquor is cooled to a temperature below about 20° C., forming a slurry containing the buprenorphine salts and the remaining mother liquor. The buprenorphine salts are filtered out of the mother liquor and rinsed with fresh isopropanol. The buprenorphine salts are then dried in a vacuum oven for at least 2 hours at a temperature ranging from about 50° C. to about 70° C. and a vacuum pressure ranging from 0 mbar to about 350 mbar.

The mother liquor from the crystallization process is combined with the first recycle phase and the second recycle phase to form a second feed solution. The second feed solution is evaporated at a temperature ranging from about 60° C. to about 70° C. and a vacuum pressure ranging from about 250 mbar to about 400 mbar until a slurry forms. Acetic acid is added to the evaporated second feed solution to adjust the pH to a value ranging from about 4.5 to about 5.

The second feed solution is contacted with the stationary phase in the chromatographic column at a temperature ranging from about 30° C. and about 40° C. A second mobile phase containing about 90% methanol and about 10% deionized water is introduced into the stationary phase after contact with the feed solution. Using the UV detector to monitor the buprenorphine and impurity content of the eluate, a second product fraction is collected.

The second product fraction is evaporated and a buprenorphine base solid is precipitated by the addition of ammonium hydroxide as described above. Buprenorphine salts are then formed from the buprenorphine base solids by dissolving in isopropanol and adding hydrochloric acid as previously described. The resulting buprenorphine salts contain less than about 0.5% by weight of combined impurities such as Impurity A and Impurity D.

(VII) Additional Exemplary Embodiment

In an additional exemplary embodiment, a feed solution is formed by dissolving an amount of crude buprenorphine composition into a sufficient amount of solvent mixture to yield a concentration of about 20 g of crude buprenorphine composition per L of solvent mixture. In this exemplary embodiment, the solvent mixture contains about 60% methanol, about 38% deionized water, and about 2% glacial acetic acid by volume. While agitating to dissolve the crude buprenorphine composition, the mixture is heated to a temperature ranging from about 35° C. to about 80° C. After filtering the mixture on a nylon 0.45 μm membrane, the resulting feed solution is maintained at a temperature ranging from about 20° C. to about 40° C. to maintain dissolution.

The feed solution is contacted with a stationary phase at a load ratio ranging from about 0.05 g to about 0.10 g of stationary phase per gram of buprenorphine contained in the crude buprenorphine composition. The stationary phase is made up of a plurality of 130 μm silica particles containing pores with a diameter of about 120 Å and a plurality of octadecyl ligands attached to the surface of the particles. The stationary phase is packed into a chromatographic column that is about 25 cm long and about 1 cm in diameter.

The mobile phase is introduced into the stationary phase after the feed solution has contacted the stationary phase. In this exemplary embodiment, the mobile phase contains about 60% methanol and about 40% water by volume. The resulting eluate is monitored using a UV detector set to wavelengths of 280 nm and 300 nm. A product fraction is collected for post-enrichment processing. The column is then flushed with 95% methanol-5% acetic acid until all of the retained color is eluted. The column is then flushed with 60% methanol, 38% deionized water, and 2% glacial acetic acid before the next feed load is introduced.

The product fraction is precipitated by adding 29 weight % ammonium hydroxide to increase the pH of the evaporated product fraction to a pH of about 9 at a temperature ranging from about 35° C. to about 50° C. The resulting slurry is cooled to a temperature below about 15° C., and the buprenorphine base solids are filtered from the slurry, using deionized water to transfer any remaining solids from the precipitation container into the filter and to rinse the filtered solids in the filter. The filtered buprenorphine base solids are then dried in a vacuum oven for at least 2 hours at a temperature ranging from about 50° C. to about 70° C. and a vacuum pressure ranging from 0 mbar and about 350 mbar.

Buprenorphine salts are formed from the dried buprenorphine base solids by dissolving the solids in isopropanol in the amount ranging from about 16 mL to about 17 mL of isopropanol per gram of buprenorphine in the buprenorphine base solids, and heating the mixture to a temperature ranging from about 40° C. to about 50° C. A 37 weight % hydrochloric acid solution is added to the heated mixture as a salt-forming agent in an amount ranging from about 0.20 g to about 0.30 g of HCl solution per g of buprenorphine in the heated mixture. The resulting mother liquor is cooled to a temperature below about 20° C., forming a slurry containing the buprenorphine salts and the remaining mother liquor. The buprenorphine salts are filtered out of the mother liquor and rinsed with fresh isopropanol. The buprenorphine salts are then dried in a vacuum oven for at least 2 hours at a temperature ranging from about 50° C. to about 70° C. and a vacuum pressure ranging from 0 mbar to about 350 mbar.

DEFINITIONS

The term "loading ratio", as defined herein, refers to the ratio of the mass of the stationary phase to the mass of the buprenorphine contained in the crude buprenorphine composition to be enriched using chromatographic methods.

The term "mobile phase", as used herein, refers to the liquid that is introduced into the stationary phase after the stationary phase has contacted the feed solution, resulting in the elution of the components of the feed solution.

The term "stationary phase", as used herein, refers to the media that adsorbs the components of the feed solution in the chromatographic column.

The term "area %", as used herein, refers to a unit of measurement calculated from analytical chromatography and is defined as the area of a particular component divided by the total area of all measured components in an eluate.

The term "buprenorphine base solid", as used herein, refers to the precipitated solid resulting from the precipitation of the evaporated product fraction. The buprenorphine base solid includes buprenorphine in a stand-alone basic amine form of the alkaloid.

The term "buprenorphine salt", as used herein, refers to a water-soluble solid form of buprenorphine in which the buprenorphine is combined with a salt-forming agent such as hydrochloric acid to form a salt such as buprenorphine hydrochloride.

The term "Impurity A", as used herein, refers to the compound 2-[17-(but-3-enyl)-4,5α-epoxy-3-hydroxy-6-methoxy-6α,14-ethano-14α-morphinan-7α-yl]-3,3-dimethyl butan-2-ol.

The term "Impurity D", as used herein, refers to the compound 17-(cyclopropylmethyl)-α-(1,1-dimethylethyl)-4,5-epoxy-3-hydroxy-6-methoxy-α-methyl-6,14-ethenomorphinan-7-methanol The term "mother liquor" refers to a mixture of buprenorphine base dissolved in an organic polar solvent such as isopropyl alcohol, formed as a by-product of the process of forming buprenorphine salts as described above.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

Example 1

Effect of Methanol Content in Mobile Phase on Enrichment of Buprenorphine

To assess the effect of the concentration of methanol in the mobile phase used in the enrichment of buprenorphine by preparative chromatography techniques, the following experiment was conducted. Stationary media consisting of 10 μm silica particles with attached C18 ligands and 120 Å pores were packed into a 10 mm×250 mm chromatography column. The amount of stationary media in the chromatography column was sufficient to result in a load ratio of 55. After an initial flush with 50 mL of 40% methanol by volume in water, the feed solution was introduced into the column at a flow rate of 3 mL/min. The feed solution contained crude buprenorphine dissolved in 40% methanol by volume in water. Acetic acid was added to the feed solution to adjust the pH of the solution to about 5.35. The feed solution contained dissolved buprenorphine as well as dissolved Impurity A and Impurity D.

After all of the feed solution had been introduced into the chromatography column, a mobile phase consisting of 88% methanol by volume in water was introduced into the stationary phase in the chromatography column at a rate of 3 mL/min. The eluate was monitored with a UV monitor to monitor the buprenorphine content of the eluate. The pre-recycle fraction of eluate collected before buprenorphine was detected in the eluate was discarded. The initial recycle fraction of eluate containing low levels of buprenorphine was collected and retained for HPLC analysis. The purified fraction of the eluate was collected beginning after a sharp increase in buprenorphine concentration in the eluate as indicated by the UV detector. Collection of the purified fraction continued until the buprenorphine detected in the eluate by the UV detector fell below a threshold level.

The experiment was repeated using a mobile phase consisting of 92% methanol by volume dissolved in water. The volumes of the pre-recycle fractions, the purified fraction, and the recycle fraction were measured for both mobile phase compositions. The fraction volumes are summarized in Table 1:

TABLE 1

Effect of Mobile Phase Composition on Fraction Volumes from Chromatographic Buprenorphine Enrichment

| | Volume of Eluate Fraction (mL) | |
| --- | --- | --- |
| Eluate Fraction | Mobile Phase 88% methanol by volume | Mobile Phase 92% methanol by volume |
| Pre-recycle | 68 | 44 |
| Recycle | 29 | 13 |
| Purified | 37 | 21 |

In addition, the feed solution and the purified fractions resulting from both mobile phase compositions were subjected to mass-spectrographic analysis to determine the relative amounts of buprenorphine, Impurity A, and Impurity D in the respective compositions. The results of this analysis are summarized in Table 2:

TABLE 2

Effect of Mobile Phase Composition on Composition of Purified Fractions from Chromatographic Buprenorphine Enrichment

| | Composition (area %) | | |
| --- | --- | --- | --- |
| | | Purified fraction | |
| Compound | Feed Solution | Mobile Phase 88% methanol by volume | Mobile Phase 92% methanol by volume |
| Buprenorphine | 96.18 | 97.29 | 98.30 |
| Impurity A | 0.08 | 0.11 | 0.00 |
| Impurity D | 0.47 | 0.59 | 0.55 |
| Yield % | — | 60 | 87 |

As indicated in Table 1, the mobile phase containing 88% methanol resulted in a more gradual elution of buprenorphine compared to the elution using a mobile phase containing 92% methanol. The volume of the pre-recycle and recycle fractions was higher for the 88% methanol mobile phase, indicating a delayed elution of buprenorphine. In addition, the volume of the purified fraction was also higher for the 88% methanol mobile phase. Referring to Table 2, the yield and purity of the purified fraction was higher for the purified fraction obtained using a mobile phase containing 92% methanol by volume.

The results of this experiment demonstrated that the use of a mobile phase containing a higher concentration of methanol in the mobile phase during the enrichment of buprenorphine using preparative chromatographic techniques resulted in a faster elution of buprenorphine, as well as a higher yield and purity of buprenorphine in the purified fraction of eluate.

Example 2

Effect of Load Ratio of Stationary Phase on Enrichment of Buprenorphine

To assess the effect of the amount of stationary phase relative to the amount of buprenorphine to be enriched by preparative chromatography techniques on the yield and purity of the enriched buprenorphine, the following experiment was conducted. Stationary media was packed into chromatography columns as described in Example 1. The amount of stationary media in the chromatography columns was sufficient to result in load ratios of 30 and 80.

Feed solutions containing buprenorphine, Impurity A and Impurity D were formed as described in Example 1, and the eluate fractions were collected as previously described using a mobile phase containing 90% methanol for both chromatographic columns. Eluate volumes were collected as previously described. The volumes of the resulting pre-recycle, recycle, and purified fractions are summarized in Table 3 for the chromatographic columns having load ratios of 30 and 80.

TABLE 3

Effect of Load Ratio on Fraction Volumes from Chromatographic Buprenorphine Enrichment

| Eluate Fraction | Volume of Eluate Fraction (mL) | |
|---|---|---|
| | Load Ratio = 30 | Load Ratio = 80 |
| Pre-recycle | 99 | 72 |
| Recycle | 25 | 5 |
| Purified | 30 | 32 |

In addition, the feed solution and the purified fractions resulting from both load ratio chromatographic columns were subjected to mass-spectrographic analysis to determine the relative amounts of buprenorphine, Impurity A, and Impurity D in the respective compositions. The results of this analysis are summarized in Table 4:

TABLE 4

Effect of Load Ratio on Composition of Purified Fractions from Chromatographic Buprenorphine Enrichment

| | Composition (area %) | | |
|---|---|---|---|
| | Feed | Purified fraction | |
| Compound | Solution | Load Ratio = 30 | Load Ratio = 80 |
| Buprenorphine | 96.18 | 97.91 | 98.38 |
| Impurity A | 0.08 | 0.07 | 0.02 |
| Impurity D | 0.47 | 0.67 | 0.50 |
| Yield % | — | 62 | 96 |

As indicated in Table 3, the chromatographic column having a load ratio of 30 resulted in a more gradual elution of buprenorphine compared to the elution from the chromatographic column having a load ratio of 80. The volume of the pre-recycle and recycle fractions was higher for a load ratio of 30, indicating a delayed elution of buprenorphine. In addition, the volume of the purified fraction was also higher for a load ratio of 30. Referring to Table 4, the yield and purity of the purified fraction was higher for the purified fraction obtained using a load ratio of 80 in the chromatographic column.

The results of this experiment demonstrated that the use of stationary phase at a higher load ratio during the enrichment of buprenorphine using preparative chromatographic techniques resulted in a faster elution of buprenorphine, as well as a higher yield and purity of buprenorphine in the purified fraction of eluate.

Example 3

Effect of Fractionation on Enrichment of Buprenorphine

To assess the effect of fractionation on the yield and purity of the enriched buprenorphine, the following experiment was conducted. Crude buprenorphine was enriched using the preparative chromatographic technique described in Example 1. Stationary media consisting of 20 µm silica particles with attached C18 ligands and 120 Å pores were packed into an 80 mm×250 mm chromatography column. The amount of stationary media in the chromatography column was sufficient to result in a load ratio of about 55.

A feed solution was formed containing crude buprenorphine dissolved in a solvent solution that included 40% methanol by volume in deionized water. Acetic acid was added to the feed solution to adjust the pH of the feed solution to about 4.0. The feed solution contained dissolved buprenorphine as well as dissolved Impurity A and Impurity D.

After an initial flush of the stationary phase with 3800 mL of 40% methanol by volume in water, the feed solution was introduced into the column at a flow rate of 4 mL/min. After all of the feed solution had been introduced in to the chromatography column, a mobile phase consisting of 90% methanol by volume in water was introduced into the stationary phase in the chromatography column at a rate of 4 mL/min. The eluate was monitored with a UV monitor to track the buprenorphine content of the eluate, and pre-recycle, recycle, and purified fractions were collected as described in Example 1. In addition, 1000 mL of eluate was collected after the purified fraction was collected and retained as a second recycle fraction.

Two enrichment trials were conducted in this experiment. In the first trial, the recycle and purified fractions were collected earlier than the appropriate time indicated by the UV detector. In the second trial, the recycle and purified fractions were collected at the appropriate times as indicated by the UV detector that was monitoring buprenorphine content in the eluate. The volumes of the resulting pre-recycle, recycle, and purified fractions are summarized in Table 5 for the two buprenorphine enrichment trials.

TABLE 5

Effect of Fractionation on Fraction Volumes from Chromatographic Buprenorphine Enrichment

| Eluate Fraction | Volume of Eluate Fraction (mL) | |
|---|---|---|
| | Trial 1 | Trial 2 |
| Pre-recycle | 2830 | 3000 |
| First Recycle | 580 | 500 |
| Purified | 950 | 850 |
| Second Recycle | 1000 | 1000 |

TABLE 5-continued

Effect of Fractionation on Fraction Volumes
from Chromatographic Buprenorphine Enrichment

| | Volume of Eluate Fraction (mL) | |
|---|---|---|
| Eluate Fraction | Trial 1 | Trial 2 |

In addition, the feed solution and the purified fractions resulting from both load ratio chromatographic columns were subjected to HPLC analysis to determine the relative amounts of buprenorphine, Impurity A, and Impurity D in the respective compositions. The results of this analysis are summarized in Table 6:

TABLE 6

Effect of Fractionation on Composition of Purified Fractions
from Chromatographic Buprenorphine Enrichment

| | Composition (area %) | | |
|---|---|---|---|
| | Feed | Purified fraction | |
| Compound | Solution | Trial 1 | Trial 2 |
| Buprenorphine | 98.64 | 99.67 | 99.73 |
| Impurity A | 0.04 | 0.15 | 0.10 |
| Impurity D | 0.19 | 0.03 | 0.03 |
| Yield % | — | 76 | 74 |

As indicated in Table 5, the pre-recycle fraction collected in Trial 1 was slightly lower than in Trial 2, due to the early collection of the first recycle fraction and the purified fraction. In addition, a higher volume of purified fraction was collected in Trial 1 due to the earlier start of its collection. Referring to Table 6, the yields of the two trials was approximately the same, but the purity of the purified fraction was slightly higher for Trial 2 due to the lower proportion of Impurity A in the purified fraction.

The results of this experiment demonstrated that the timing of collection of the recycle and purified eluate fractions had minimal effect on the overall yield of the purified fractions. Further, early collection of the recycle and purified fractions resulted in slightly less pure buprenorphine, due to the presence of a slightly higher proportion of Impurity A.

Example 4

Effect of Concentration of Feed Solution on Enrichment of Buprenorphine

To assess the effect of the concentration of crude buprenorphine in the feed solution on the yield and purity of the buprenorphine enriched by preparative chromatography techniques, the following experiment was conducted. Crude buprenorphine was enriched using the preparative chromatographic technique described in Example 3.

Two trials were conducted with two different concentrations of feed solution. The compositions of the two feed solutions are summarized in Table 7:

TABLE 7

Composition of Feed Solutions

| Eluate Fraction | Trial 1 | Trial 2 |
|---|---|---|
| pH | 4.3 | 4.0 |
| Crude Buprenorphine Concentration (g/L) | 17.5 | 28.5 |
| Volume (mL) | 690 | 393 |

The volumes of the resulting pre-cycle, recycle, and purified fractions are summarized in Table 8 for the two buprenorphine enrichment trials:

TABLE 8

Effect of Feed Solution Concentration on Fraction Volumes
from Chromatographic Buprenorphine Enrichment

| | Volume of Eluate Fraction (mL) | |
|---|---|---|
| Eluate Fraction | Trial 1 | Trial 2 |
| Pre-recycle | 2450 | 2633 |
| First Recycle | 0 | 755 |
| Purified | 1655 | 800 |
| Second Recycle | 1120 | 1000 |

In addition, the feed solutions and the purified fractions resulting from both load ratio chromatographic columns were subjected to HPLC analysis to determine the relative amounts of buprenorphine, Impurity A, and Impurity D in the respective compositions. The results of this analysis are summarized in Table 9:

TABLE 9

Effect of Feed Solution Concentration on Composition of Purified
Fractions from Chromatographic Buprenorphine Enrichment

| | Feed Solution | | Purified fraction | |
|---|---|---|---|---|
| Compound | Trial 1 | Trial 2 | Trial 1 | Trial 2 |
| | Composition (area %) | | | |
| Buprenorphine | 98.64 | 98.64 | 99.49 | 99.74 |
| Impurity A | 0.04 | 0.04 | 0.18 | 0.03 |
| Impurity D | 0.19 | 0.19 | 0.06 | 0.08 |
| | Yield % | | | |
| Pre-recycle fraction | — | — | 4 | 0 |
| Recycle + Purified fraction | — | — | 95 | 99 |

As indicated in Table 9, about 4% of the total yield of buprenorphine was eluted in the pre-recycle fraction collected during Trial 1. This was likely due to the total volume of the feed solution in Trial 1 (see Table 8) exceeding the dead volume of the chromatographic column, which was about 500 mL for this experiment. As a result, 4% of the buprenorphine was eluted before the UV detector triggered the collection of the first recycle fraction. No buprenorphine was eluted in the pre-recycle fraction in Trial 2, most likely because the total volume of the feed solution in this trial (see Table 8) was under the dead volume of the chromatographic column.

The results of this experiment demonstrated that the concentration of buprenorphine in the feed solution had an effect on the yield of buprenorphine in the purified fraction. In particular, when the total volume of the feed solution exceeded the dead volume of the chromatographic column due to a low concentration of feed solution, the buprenorphine in the feed solution may not have sufficient opportunity to be adsorbed on the stationary media, causing loss of buprenorphine in the pre-recycle eluate fraction.

Example 5

Effect of Evaporated Eluate Methanol Content on the Precipitation of Buprenorphine Base Solids To assess the effect of the concentration of methanol in the purified evaporated eluate on the yield of buprenorphine base solids resulting from precipitation, the following experiment was conducted. Purified fractions resulting from the enrichment of buprenorphine using the preparative chromatography techniques described in Example 3 were evaporated to a concentrated solution. The concentration solutions were then treated with ammonium hydroxide to reduce the pH of the concentrated solution to 8.8-9.2. The resulting slurry was then cooled to a temperature of less than about 25° C. After cooling, the resulting buprenorphine base solids were filtered and dried.

Two trials were conducted, in which 19% methanol and 44% methanol by weight was retained in the concentrated solutions of Trials 1 and 2 respectively prior to precipitation. The purity of buprenorphine in the resulting buprenorphine base solids was determined using HPLC analysis. In addition, the concentration of buprenorphine in the mother liquor remaining after the buprenorphine base solids had been filtered out was determined using mass spectrometry. The results of this experiment are summarized in Table 10:

TABLE 10

Effect of methanol content on precipitation of evaporated purified fraction

| | Trial 1 | Trial 2 |
|---|---|---|
| Concentration of purified fraction after evaporation (g/L) | 11.6 | 24.0 |
| Methanol in concentrate (wt %) | 19 | 44 |
| Concentrate purity (area %) | 99.00 | 99.05 |
| Final pH during precipitation | 8.81 | 9.12 |
| Solids purity, (area %) | 99.51 | 99.87 |
| Concentration in mother liquor (g/L) | 0.24 | 0.20 |

As indicated in Table 10, the concentration of methanol in the evaporated purified fractions had little effect on the purity of the resulting buprenorphine base solids after precipitation. In addition, the concentration of methanol in the evaporated purified fractions did not significantly influence the amount of buprenorphine remaining in the mother liquor. Although there was a slightly lower purity in the solids formed during Trial 1, this was likely due to the tendency of the solids in this trial to form sticky agglomerates that were difficult to transfer, resulting in higher transfer losses of buprenorphine base solid.

The results of this experiment demonstrated that the concentration of methanol in the evaporated purified fraction had little effect on the purity of the resulting buprenorphine base solids. However, a higher concentration of methanol of around 40-50% methanol by weight in the evaporated purified fraction inhibits the tendency of the resulting solids to form sticky agglomerates, thereby reducing losses due to the transfer of slurries during the precipitation process.

Example 6

Removing Color Using Preparative Chromatography

Another application was the removal of color using chromatography. For these cases the levels of Compound A and Impurity D were already within specification. The feed though had amber and purple color that needed to be adsorbed away from the buprenorphine. These color bodies have yet to be identified. To assess the effect of the concentration of methanol in the mobile phase used in the removal of the color from buprenorphine by preparative chromatography techniques, the following experiment was conducted. Stationary media consisting of 130 μm silica particles with attached C18 ligands and 120 Å pores were packed into a 10 mm×250 mm chromatography column. The amount of stationary media in the chromatography column was sufficient to result in a load ratio of 0.05. After an initial flush with 50 mL of 40% methanol by volume in water, the feed solution was introduced into the column at a flow rate of 3 mL/min. The feed solution contained crude buprenorphine dissolved in 55-70 wt % methanol by volume in water. Acetic acid was added to the feed solution at 1 wt % to adjust the pH of the solution to about 5.35. The feed solution contained dissolved buprenorphine with about 1% of impurities.

During the loading of the feed, the buprenorphine began to elute from the column as indicated by the rise in UV. This was collected as the product fraction. After all of the feed solution had been introduced into the chromatography column, a mobile phase consisting of 60% methanol by volume in water was introduced into the stationary phase in the chromatography column at a rate of 3 mL/min. Collection of the purified fraction continued until the buprenorphine detected in the elution by the UV detector fell below a threshold level. After the product fraction was collected, the column was flushed with a mobile phase consisting of 95% methanol and 5% acetic acid to elute the adsorbed color.

The resulting buprenorphine product fraction was then heated to 50-60° C. The solids were precipitated by adding 29% ammonium hydroxide until the pH was 8.0-9.0. The resulting solids were then washed with water at 2-5 ml per g of buprenorphine. The solids were dried at 50-70° C. with −15 to −25 in Hg vacuum until a constant weight was attained.

In Table 11 below, the trials are compared with the appearance of the resulting buprenorphine base. Since the USP and EP specify only an appearance test to be white to almost-white, an independent reviewer determined if the solids would pass the test.

TABLE 11

Effect of methanol content on the removal of color from buprenorphine

| | Methanol content in feed, wt % | Area % of buprenorphine base solids | % Yield from crude feed to purified solids | Passing appearance as white/almost-white? |
|---|---|---|---|---|
| Trial 1 | 45 | 99.97 | 93 | Yes |
| Trial 2 | 55 | 99.86 | 97 | Yes |
| Trial 3 | 60 | 99.89 | 93 | No |
| Trial 4 | 68 | 99.90 | 87 | No |

Each of the trials shown above was able to attain at least 99.85 area % buprenorphine base in the solids. The yield was at least 87% in each trial, with the losses coming in what was retained on the column during the 95% methanol-5% acetic flush and in the mother liquor. Trial 4 had the lowest yield due to its highest methanol content of 68% causing a greater solubility of buprenorphine base in the mother liquor. The lower the methanol content used in the feed preparation resulted in a greater likelihood of attaining the desired appearance. Minimizing the methanol essentially caused more of the color to remain adsorbed in the column. That is why Trials 1 and 2 had passing appearance in the solids.

What is claimed is:

1. A method for enriching buprenorphine relative to 2-[17-(but-3-enyl)-4,5α-epoxy-3-hydroxy-6-methoxy-6α,14-ethano-14α-morphinan-7α-yl]-3,3-dimethylbutan-2-ol and 17-(cyclopropylmethyl)-α-(1,1-dimethylethyl)-4,5-epoxy-3-hydroxy-6-methoxy-α-methyl-6,14-ethenomorphinan-7-methanol in a buprenorphine product, the method comprising:
   a. forming a first feed solution by dissolving a crude buprenorphine composition comprising buprenorphine, 2-[17-(but-3-enyl)-4,5α-epoxy-3-hydroxy-6-methoxy-6α,14-ethano-14α-morphinan-7α-yl]-3,3-dimethylbutan-2-ol, and 17-(cyclopropylmethyl)-α-(1,1-dimethylethyl)-4,5-epoxy-3-hydroxy-6-methoxy-α-methyl-6,14-ethenomorphinan-7-methanol in a solvent mixture comprising an acid, a first organic polar solvent, and water;
   b. contacting the first feed solution with a stationary phase;
   c. introducing into the stationary phase a first mobile phase comprising a second organic solvent and water, wherein the amount of the second organic solvent is at least 85% (V/V) of the mobile phase; and,
   d. eluting from the stationary phase a first product fraction comprising between about 80% and 100% of the amount of buprenorphine contained in the crude buprenorphine composition.

2. The method of claim 1, wherein the acid is chosen from acetic acid, malic acid, tartaric acid, sulfuric acid, formic acid, oxalic acid, lactic acid, hydrochloric acid, hydrobromic acid, phosphoric acid, phosphorous acid, nitric acid and combinations thereof; the first organic polar solvent is chosen from ethanol, methanol, propanol, isopropanol, butanol, t-butanol, acetonitrile and combinations thereof; and the second organic polar solvent is chosen from ethanol, methanol, propanol, isopropanol, butanol, t-butanol, acetonitrile and combinations thereof.

3. The method of claim 1, wherein the acid is acetic acid; the amount of acetic acid ranges between about 0.1 and about 10 mL of pure acetic acid per gram of the crude buprenorphine composition; the first organic polar solvent is methanol; and the second organic polar solvent is methanol.

4. The method of claim 1, wherein the mass of the stationary phase ranges between about 50 and about 250 times the mass of crude buprenorphine composition dissolved in the first feed solution; and the ratio of the mass of buprenorphine in the product fraction and the combined mass of 2-[17-(but-3-enyl)-4,5α-epoxy-3-hydroxy-6-methoxy-6α,14-ethano-14α-morphinan-7α-yl]-3,3-dimethylbutan-2-ol, and 17-(cyclopropylmethyl)-α-(1,1-dimethylethyl)-4,5-epoxy-3-hydroxy-6-methoxy-α-methyl-6,14-ethenomorphinan-7-methanol in the first product fraction is at least 200:1.

5. The method of claim 1, wherein the stationary phase comprises a plurality of particles with attached ligands, wherein the particles comprise a material chosen from silica, polymers, zirconium oxide, and titanium, and wherein the ligands are chosen from octadecyl ligands, octyl ligands, butyl ligands, tricosane ligands, cyano ligands, phenyl ligands, and combinations thereof; and the size of the particles range between about 15 and about 50 microns in diameter.

6. The method of claim 1, further comprising forming a first buprenorphine base solid by evaporating the first product fraction to form a first slurry and increasing the pH of the first slurry to about 9 by adding an amount of a first proton-acceptor.

7. The method of claim 6, further comprising forming a first buprenorphine salt and a first mother liquor by contacting the first buprenorphine base solid with a third organic solvent and a first salt-forming agent, wherein the first mother liquor comprises buprenorphine, the third organic polar solvent, and the first salt-forming agent.

8. The method of claim 7, wherein the third organic polar solvent is chosen from ethanol, methanol, propanol, isopropanol, butanol, t-butanol, acetonitrile and combinations thereof; the third organic polar solvent is isopropanol; and the first salt-forming agent is chosen from hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalic acid, fumaric acid, propionic acid, aspartic acid, glutamic acid, benzoic acid, methyl fluoride, methyl chloride, methyl bromide, and methyl iodide.

9. The method of claim 1, further comprising eluting from the stationary phase a first recycle fraction prior to eluting the first product phase, wherein the first recycle fraction comprises between about 1% and about 20% of the amount of buprenorphine contained in the crude buprenorphine composition.

10. The method of claim 9, further comprising eluting from the stationary phase a second recycle fraction after eluting the first product phase, wherein the second recycle fraction comprises between about 1% and about 20% of the amount of buprenorphine contained in the crude buprenorphine composition.

11. The method of claim 10, further comprising:
   a. forming a second feed solution by evaporating at least one of the first recycle fraction, the second recycle fraction, the first mother liquor, and combinations thereof;
   b. contacting the second feed solution with the stationary phase;
   c. introducing into the stationary phase a second mobile phase comprising a fourth organic polar solvent and water, wherein the amount of the fourth organic polar solvent is at least 85% (V/V) of the second mobile phase; and,
   d. eluting from the stationary phase a second product fraction comprising between about 80% and 100% of the amount of buprenorphine contained in the second feed solution.

12. The method of claim 11, wherein the fourth organic polar solvent is chosen from ethanol, methanol, propanol, isopropanol, butanol, t-butanol, acetonitrile and combinations thereof.

13. The method of claim 11, further comprising forming an additional amount of buprenorphine base solid by evaporating the second product fraction to form a second slurry and increasing the pH of the second slurry to about 9 by adding an amount of a second proton-acceptor.

14. The method of claim 13, further comprising forming an additional amount of buprenorphine salt by contacting the additional amount of buprenorphine base solid with a fifth organic polar solvent and a second salt-forming agent.

15. The method of claim 14, wherein the fifth organic polar solvent is chosen from ethanol, methanol, propanol, isopropanol, butanol, t-butanol, acetonitrile and combinations thereof; and the second salt-forming agent is chosen from hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalic acid, fumaric acid, propionic acid, aspartic acid, glutamic acid, benzoic acid, methyl fluoride, methyl chloride, methyl bromide, and methyl iodide.

16. The method claim 1, wherein the additional amount of buprenorphine salt comprises less than about 0.1% by weight of combined 2-[17-(but-3-enyl)-4,5α-epoxy-3-hydroxy-6-methoxy-6α,14-ethano-14α-morphinan-7α-yl]-3,3-dimethylbutan-2-ol and 17-(cyclopropylmethyl)-α-(1,1-dimethylethyl)-4,5-epoxy-3-hydroxy-6-methoxy-α-methyl-6,14-ethenomorphinan-7-methanol.

17. The method of claim 1, wherein the buprenorphine salt comprises less than about 0.05% by weight of combined 2-[17-(but-3-enyl)-4,5α-epoxy-3-hydroxy-6-methoxy-6α,14-ethano-14α-morphinan-7α-yl]-3,3-dimethylbutan-2-ol and 17-(cyclopropylmethyl)-α-(1,1-dimethylethyl)-4,5-epoxy-3-hydroxy-6-methoxy-α-methyl-6,14-ethenomorphinan-7-methanol.

18. The method of claim 1, wherein the buprenorphine salt comprises less than about 0.01% by weight of combined 2-[17-(but-3-enyl)-4,5α-epoxy-3-hydroxy-6-methoxy-6α,14-ethano-14α-morphinan-7α-yl]-3,3-dimethylbutan-2-ol and 17-(cyclopropylmethyl)-α-(1,1-dimethylethyl)-4,5-epoxy-3-hydroxy-6-methoxy-α-methyl-6,14-ethenomorphinan-7-methanol.

19. The method of claim 1, wherein color is removed from the buprenorphine.

20. The method of claim 1, wherein any adsorbed color is removed from the stationary phase with a mobile phase consisting of an organic solvent and an organic acid.

* * * * *